United States Patent [19]
Herzberg

[11] Patent Number: 4,893,618
[45] Date of Patent: Jan. 16, 1990

[54] EXTERNAL FIXATION APPARATUS
[76] Inventor: Wolfgang Herzberg, Holmer Strasse 165, D-2000 Wedel/Holstein, Fed. Rep. of Germany
[21] Appl. No.: 188,398
[22] PCT Filed: Aug. 26, 1987
[86] PCT No.: PCT/EP87/00486
§ 371 Date: Apr. 21, 1988
§ 102(e) Date: Apr. 21, 1988
[87] PCT Pub. No.: WO88/01488
PCT Pub. Date: Mar. 10, 1988
[30] Foreign Application Priority Data
Aug. 26, 1986 [DE] Fed. Rep. of Germany ....... 3628972
[51] Int. Cl.⁴ ............................................. A61F 5/04
[52] U.S. Cl. .................. 606/54; 128/92 ZZ; 128/92 ZW
[58] Field of Search .................. 128/82.1, 87 R, 89 R, 128/90, 92 Z, 92 ZZ, 92 ZY, 92 ZK, 92 ZW; 285/179

[56] References Cited
U.S. PATENT DOCUMENTS
2,878,038 3/1959 Noland ........................... 285/179 X
3,877,424 4/1975 Murray ............................... 128/92 Z
4,584,995 4/1986 Koeneman ......................... 128/92 Z
4,604,996 8/1986 Nunamaker et al. ............. 128/87 R
4,624,249 11/1986 Alvarez .......................... 128/92 ZZ FOREIGN PATENT DOCUMENTS
2405063 5/1979 France .
848008 7/1981 U.S.S.R. .............................. 128/92 Z
1146017 3/1985 U.S.S.R. .............................. 128/92 X
2086231 5/1982 United Kingdom .
2146533 4/1985 United Kingdom .............. 128/92 Z
86/02822 5/1986 World Int. Prop. O. ........ 128/92 Z OTHER PUBLICATIONS
De Puy Mfg. Co. Catalogue, pg. 55, 1936.
Journal of Bone and Joint Surgery, Manipulation and External Fixation of Metacarpal Fractures, vol. 63A, No. 8, 10/1981, pp. 1289–1291.

Primary Examiner—Mickey Yu
Assistant Examiner—Kevin G. Rooney
Attorney, Agent, or Firm—Toren, McGeady & Associates

[57] ABSTRACT

The external apparatus for fixing bone fragments consists of a tube-shaped portion, of which the internal space is filled with glass fibre. The fixing tube is secured by means of nails or screws (12) to the bone fragments to be fixed, whereby a rapid hardening material is introduced into the closed tube system after completion of assembly. After setting, a plastic-glass fibre composite is obtained which has excellent strength properties and is ideally suited for use as an external fixation apparatus.

26 Claims, 7 Drawing Sheets

EXTERNAL FIXATION APPARATUS

The present invention relates to an external fixation apparatus comprising at least one flexible tube-shaped portion which is disposed externally of the patient opposite the bone fragments to be fixed and which is connected with the wires, nails or screws secured in the various bone fragments, wherein the tube-shaped portion filled with a hardenable material, after the material is hardened, forms a rigid frame with the wires, nails or screws which holds the bone fragments together in a desired position for the union of the same.

External fixation apparatuses serve for the orthopedic fixation and the holding together of bone fragments. Fractured bones are fixed in their position relative to one another with an external fixation apparatus so that the healing can take place in the correct position. For this purpose, bone nails, preferably with a thread, e.g. Schanz's screws or bridging rods, are inserted into or through the bone and, at their ends projecting from the body, interconnected by at least one rod-shaped member, e.g. a sliding rod or a guide rod. This connection is brought about with the aid of tightening means that are constructed as shims, articulation pieces and, if necessary, as ball-and-socket joints, as coupling means or as grips or the like. A frame structure can thus be formed, with the aid of which the bone fragments can be rigidly fixed and held.

Known tightening means consist of non-oxidizing steel. When the fixation apparatus is applied and the rods are tightened, the entire frame structure is relatively loose, wobbly and displaceable into itself since the rods to be reciprocally held have to be slackened in the tightening means so that they can be brought into the correct position. Hence the application of a fixation apparatus can, in the end, not be carried out by a single person, but additional assistants are needed for holding the joints and double joints as well as the frame until, subsequent to the positioning, the tightening and fixing can ultimately be carried out. In order to facilitate this work, separate tightening devices may be employed. However, since steel has a very high elasticity coefficient and a smooth surface, it is not possible to obtain only a weak clamping by tightening a clamping bolt; on account of the high elasticity coefficient, already a slight turning of a setscrew brings about a very substantial change in the gripping pressure. Consequently, when fitting the fixation apparatus, the rods, bones nails or screws can only lie loosely within the tightening means. Added hereto is the circumstance that the components and elements used for the fixation apparatus, due to their material selection, impair X-rays. Moreover, the production costs of fixation apparatuses constructed in this fashion are very high.

The utlization of metal components predominates from which the fixation apparatus is assembled by the surgeon depending on individual requirements. In order to obtain a radiotransparency with fixation apparatuses, use is also made of components fabricated from non-metallic materials. Thus, from the DE-A-27 45 504, a device for the immobilization and/or support of human or animal limbs is known which possesses connecting members that are oppositely located in pairs and accommodate at least one bone screw or one bone nail each, which, via clamping members, are connected by means of connecting rods or threaded rods. The connecting members, the clamping members and the connecting rods as well as the integrated tighteners consist in this case of fiber reinforced thermoplastics.

Furthermore, from the DE-A-31 41 909, an orthopedic fracture fixation device with at least one elongate part located externally of the patient is known, which is connected by means of fracture pins or the like that can be secured in the various fragments of the broken bone, wherein the elongate part and the pins form a rigid frame holding the fragments in the desired position for their union. The elongate part located externally of the patient, which is secured to the various fragments of the fractured bone by means of bone pins, comprises an elongate carrier of flexible shape which is filled with a hardenable material which is disposed inside the carrier in an inactive free-flowing state.

Fixation apparatuses in which preformed and rigid components are employed are very expensive in the production of the kit required in each particular case. A specific kit only possesses an applicability which is restricted to specific fractures, a circumstance which entails the maintenance of stocks and the storage of a comprehensive assortmennt of the individual components. After repeated use threaded components show signs of wear. If metallic materials are used, the radiographic checking of the healing of the fracture is possibly significantly impaired. With each patient who has been fitted with a fixation device, a part of the kit in stock is blocked for weeks, which necessitates a further extension of a maintenance of stocks of the individual components. The unreliable patient and the patient who passes through fails to return to the hospital which has been the prime supplier. The fitted components do not return into the possession of the hospital, whereby a substantial loss of components comes about. In addition, the rigid kit systems force to a varying extent an arrangement of fracture fragments as well as of the external fixation device which is in conformity with the coordinates. In order to arrive at a good operation result under these constrains, not infrequently a great deal of experience as well as both spatial and planning imagination are called for.

In the case of external fixation devices consisting of flexible components which, by thermosetting or hardening, are transformed into a rigid system, use is made of a hose filled with liquid plastic which, however, can only after the fixation of the nails on the bone, be pushed over the free ends of the same. For, in a reversed sequence, the points of the nail would, since such a hose is not sterilizable, both spread an infection as well as transport monomeric plastic into the organism. Due to this prior condition, a parallel arrangement of the nails is necessary, which comes close to the constraints imposed upon the surgeon by the rigid system. A fixation in more than one plane, which is at all times to be strived for on account of mechanical considerations, cannot be managed with a hose. To a varying degree all homogeneous plastic materials possess only a minor breaking strength with, at the same time, a low elasticity. From this results the necessity of large cross sections of the supporting fixation device hose, without any guarantee that the fixation device will not break after all at some time or other due to a peak load. Added hereto is the circumstance that a thorough blending or mixing of the plastic components in an already filled hose entails several disadvantages. The risk of an incomplete mixing with the consequence that soft and more easily deflectable hose sections are obtained after the termination of the operation is relatively great. Over and above that, an imperfect mixing increases the proportion of remaining and possibly toxic monomers in the fixation device. An as good as possible thorough blending is possible only in a soft supporting hose which can readily be pressed in. This has as a consequence that an as constant as possible cross section of the plastic cannot be ensured, especially not if the fixation device hose is installed in numerous spirals. The thorough mixing of the components of which the hardenable material consists when using a hose which is already filled does, to all intents and purposes, invariably lead to an escape of plastic material from the points punctured by the nail and, thereby, to an incalculable loss of substance and stability. When hardening or curing by supplying heat or radiation, the following additional problems arise: Only surface coatings can be polymerized by means of radiation. A completely filled hose is hardly polymerizable by radiation. Infrared radiation is intended to penetrate hose systems located close to the skin level—2 to 5 cm—but not to warm the skin itself. It is true that to protect a patient against ultraviolet radiation is simpler than against infrared radiation, however, with both types of radiation an extensive illumination of the hose system must be achieved. This has to take place simultaneously with a fluoroscopy and the resetting maneuver by the surgeon, an overall arrangement which is possibly difficult to put into effect from a technical point of view. In the case of a photosensitive plastic which is protected by a light-proof sheet, the piercing of the hose by fixing nails may already trigger off the hardening process. A final bone resetting is held in position by the surgeon for approximately 5 minutes. The fixation device must have hardened within this period. Longer hardening or curing times increase the exposure to X-rays and harbour the risk of a more likely worse resetting result due to the surgeon tiring.

The present invention solves the technical problem of providing an external fixation apparatus of the aforementioned type, with which a simple manipulation without any imposed levels of work with the possibility of effecting positional corrections of the fixation hose or tube prior to the hardening of the filler material without any displacements of straightened bone fragments occurring so that also complicated bone fractures, i.e. a large number of bone fragments, can be maintained in the correct position until the filling material is set, whereby a universal applicability is ensured and a limited maintenance of stocks with a small assortment of the fixation apparatus components is possible. In addition, it is intended that a radiotransparency as well as a great stability and high elasticity exists already in the case of small cross sections. It is furthermore the object of the invention to provide a tube-shaped portion for an external fixation apparatus which may at the same time be used as a mold for the plastic to be cured and the hose body of which forms an intimate bond with the set plastic.

This technical problem is solved by the features characterized in claim 1.

By the use of a tube-shaped portion in an external fixation apparatus comprising a plastic hose with an inserted glass fiber hose or a glass fiber reinforced plastic or of a glass fiber fabric embedded in a plastic, all the shortcomings to which the known external fixation devices are subject, are remedied. A tube-shaped portion constructed in such a way is filled with quick-curing synthetic resin subsequent to the assembly having been carried out so that, from a flexible, easily handled material, a rigid external fixation apparatus is obtained which, moreover, is radiotransparent, is very inexpensive and, when employing various hose thicknesses and glass fiber fillings, can be universally employed so that every required strength is obtained. Using the external fixation apparatus as a disposable article circumvents the problem of wear and tear. The use of a plastic-glass fiber composite in an external fixation appartus means that for the first time a material is employed that enables the operating surgeon for the first time to have at his disposal a system for the orthopedic fixation as well as for holding the bone fragments together with which the requirements stipulated for an external fixation apparatus are met. Particularly by the use of a glass fiber filled spiral hose, a fixation apparatus hose is obtained which, during the assembly of the fixation apparatus, allows itself to be readily deformed and bent aside in different planes without any cross-sectional changes occurring at the bending points, which, on the one hand, is to be ascribed to the specific inherent stability of the fixation apparatus hose and, on the other hand, to the circumstance that a glass fiber fabric hose is inserted into the plastic hose.

When shaping and fitting the fixation apparatus hose into position, it is precisely this deformation resistance which ensures an unimpeded passage of the introduced free-flowing plastic material which, following the thorough mixing of the components outside the hose, is injected into the same. Within the fixation apparatus hose a "thorough blending" of woven glass fibers with the synthetic resin then takes place and a plastic-glass fiber composite comes into existence. The glass fibers anchored in the material of the fixation apparatus hose, or the glass fiber fabric hose inserted into the hose of pure plastic increase the ultimate strength of the tube-shaped portion which is preferably constructed as a spiral hose and which, on account of this configuration, can be bent aside without difficulty and thus installed. Due to the high resistance to fracture, hoses having small cross sections may also be employed. Also, when injecting the preferably quick-curing synthetic resin mass, an escape of this plastic material from the nail perforations in the walls of the fixation apparatus hose is not possible since the perforations formed in the walls of the fixation apparatus hose when the fixing nails or screws are introduced within the penetration area of the fixing nail automatically seal themselves again, this automatic sealing being assisted by the glass fibers incorporated into the hose material, by the glass fiber filling or by the inserted glass fiber hose which constitute a kind of sealing safeguard, it being advantageous in this case if tube-shaped portions are employed which consist of a very fine-meshed glass fiber fabric embedded in a plastic or of a ver fine-meshed glass fiber fabric hose. On account of this a very thin-walled hose may also be used.

According to a further embodiment of the invention the external fixation apparatus consists of a single tube-shaped portion fabricated from a glass fiber hose inserted into a plastic hose or from a glass fiber reinforced plastic or from a glass fiber fabric embedded in a plastic, this tube-shaped portion being routed in various planes and directions across the bone fragments and connected with the bone fragments with the aid of the wires, nails or screws. The two free ends of this tube-shaped portion are interconnected via a preferably Y-shaped or T-shaped connecting union which is provided with a sealable filling aperture for the hardenable material. It is possible in this manner to fix fragments of fractured bones, e.g. of phalanxes, with a single tube-shaped portion while making use of wires, nails or screws without it being necessary to employ an expensive frame for this. Subsequent to the quick-curing synthetic resin having been introduced into the tube-shaped portion and following the curing of the synthetic resin, a firm system which is rigid in itself is obtained so that a favorable healing process is achieved.

Furthermore, the possibility exists of joining several tube-shaped portions together so as to form a frame, all the tube-shaped portions being interconnected via tubular connecting unions in such a way that the inner spaces of all the tube-shaped portions intercommunicate, the hose system thus constructed having at least one sealable filling aperture provided for the hardenable material. Over and above that there also exists the possibility of combining several tube-shaped portions of the hose system into groups, the hose system formed by each group being provided with at least one sealable filling aperture for the hardenable material.

It is possible in this manner to optimally adapt such an external fixation apparatus to the various requirements while use is made of different types of connecting unions. In this case, connecting unions bent aside at 90° or at 180°, as well as T-shaped, Y-shaped and cross-type connecting unions are employed as two-dimensional connecting pieces. In hose sections which span the fractures, preferably no connecting unions should be incorporated since these might possibly turn into weak points of the stability.

In order to ensure an adequate transfer of force from the hose system to the fixing nails or screws, in the case of larger nail or screw cross sections and, at the same time, of a greater rise in forces as, for instance, infractures of the lower extremity, it no longer suffices to simply drill nails or screws through the hose, especially as a bending aside and embedding is no longer possible due to the larger nail cross section. Rather, the nail or the screw will have to be anchored on the hose system with the aid of a fixation means, such a fixation means having to meet the following requirements:

It must be possible to mount it at any point whatever of the hose;

It must be capable of holding the nail or screw in a rotationally stable manner;

It has itself to be firmly secured in the glass fiber plastic of the hose in order to distribute the frictional connection;

It has to be universally employable to the highest degree for different nail or screw cross sections;

The fixation means must be radiotransparent.

All these prior conditions are met by a fixation member comprising two shell-shaped parts encasing the tube-shaped portions which complement one another so as to form a tubular structural element, wherein each shell-shaped part has, on at least two oppositely located sides, shell-like-configured sections which complement one another so as to form two mutually aligned attachment studs and serve to receive a screw or a nail, the shell-shaped sections, on their outer wall, being provided with an external thread for accommodating a coupling nut which overlaps a compression ring. Apart from screws provided with a thread extending over the full length of the screw shank, it is also possible to use screws provided with a thread on the drilled-in section while the remaining shank is constructed in a plain fashion. Even when the thread is constructed so as to be continuous on the screw shank, these screws are handled as if no thread exists. The fitting of the shell-like configured parts of the fixation member which acts like a gripping device is carried out subsequent to the nails or screws having been drilled in.

According to a further embodiment of the invention, the fixation member consists of a tube provided with an external thread passed through two oppositely located and mutually aligned perforations in the wall of the tube-shaped portion which, within its inner space, accommodates a nail or a screw, the threaded tube being made to project on both sides with a section from the tube-shaped portion and, on its sections within the area of its extremities, carries one coupling nut each which engages with the external thread of the threaded tube which overlaps a compression ring that can be brought into abutment when tightening the coupling nut fitted to the end of each section of the threaded tube provided on the outer wall surface of the nail or screw arranged within the threaded tube, wherein the threaded tube, on its section facing the bone fragments, carries a threaded coupling clamp seated upon the external fixation apparatus with a stud, spike or the like engaging into the wall of the tube-shaped portion and, on its other section, an unthreaded coupling clamp with a stud, spike or the like engaging into the wall of the tube-shaped portion, the unthreaded coupling clamp on the threaded tube being retained by means of a nut.

These two differently constructed fixation members are adapted to the different nail and screw cross sections by the employment of appropriate compression rings and thus meet the requirements stipulated for the fixation member.

Advantageous embodiments of the invention are characterized in the subclaims.

In the following the subject matter of the invention is explained in the drawings.

Figure 1:
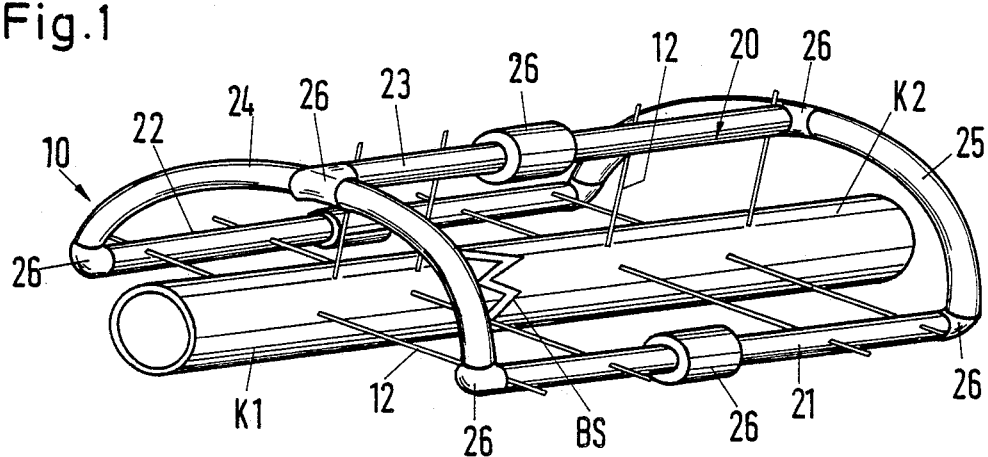
FIG. 1 shows, in a diagrammatical view, an external fixation apparatus consisting of several interconnected tube-shaped portions applied to two bone fragments.
Figure 2:
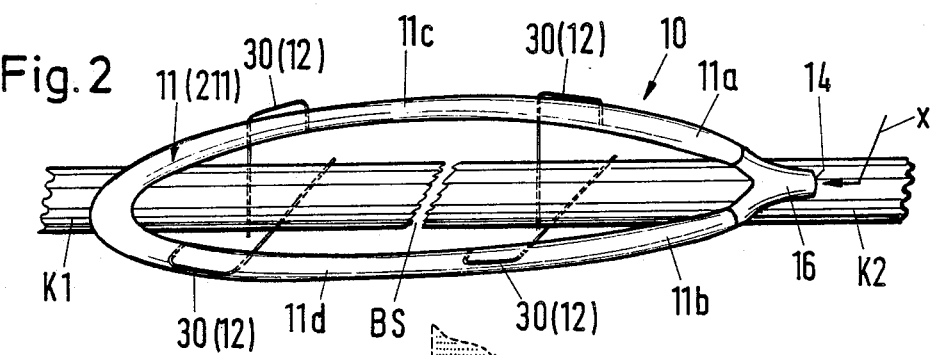
FIG. 2 shows, in a diagrammatical view, an external fixation apparatus consisting of a tube-shaped portion interconnected at the ends and secured to two bone fragments by means of Kirschner wires.

The external fixation apparatus shown in FIGS. 1 and 2 is identified by 10. This external fixation apparatus 10 consists of a tube-shaped portion 11 or 211 in the form of a hose system 20 of several individual interconnected hose sections, the two ends of which intercommunicate (FIG. 2). This tube-shaped portion 11 or 211 constitutes the fixation apparatus hose; its wall is identified by 111a or 211a. The securing of the tube-shaped portion 111 or 211 to two bone fragments identified by K1 and K2 is effected with the aid of wires, nails or screws 12.

The tube-shaped portion 211 consists of a hose body 212 fabricated from a flexible plastic which possesses a certain elasticity. This hose body 212 is filled with glass fibers or other mineral fibers. This filling with glass fibers is carried out in the form of a hose or stocking 215 fabricated from a glass fiber fabric (FIG. 12) inserted into the inner space of the hose body 212. According to FIG. 13, it is also possible for several individual glass fiber fabric hoses 215,216,217 to be inserted into the inner space of the hose body 212, so that, when viewed in a cross section, several layers of glass fiber fabric result. According to a further embodiment per FIGS. 15 and 16, so many glass fiber fabric hoses are inserted into the inner space of the hose body 212 that the inner space of the hose body 212 is filled completely with glass fibers. Moreover, the possibility also exists of employing a glass fiber fabric mat in lieu of the glass fiber fabric hoses that is inserted in a folded or rolled-up state into the inner space of the hose body 212. When several glass fiber fabric hoses are used, all hoses may have an identical thickness; it is also possible, however, to make use of varying thicknesses.

Figure 17:
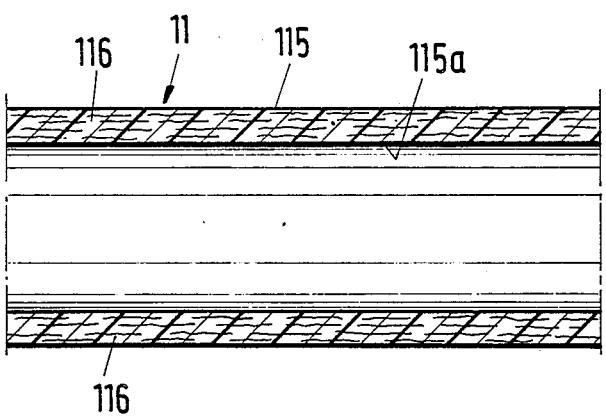
FIG. 17 shows, in an enlarged section, a section of a tube-shaped portion of a hose body fabricated from a plastic with glass fibers embedded in the same.
Figure 18:
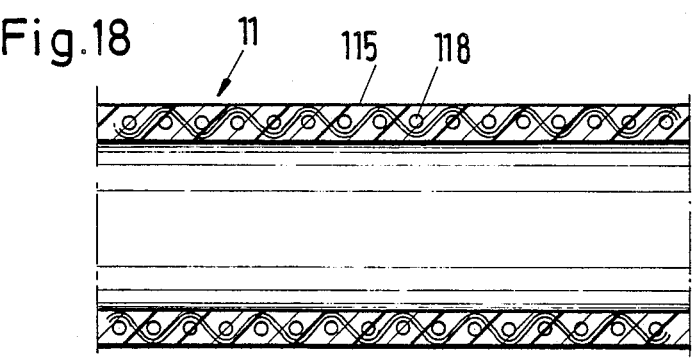
FIG. 18 shows, in an enlarged vertical section, a section of a tube-shaped portion of a hose body fabricated from a plastic with a glass fiber fabric incorporated into the same.

According to a further embodiment per FIGS. 17 and 18, the tube-shaped portion 11 consists of a glass fiber reinforced plastic or of a glass fiber fabric embedded in a plastic material. According to this the tube-shaped portion 11 comprises a hose body 115 fabricated from a flexible plastic material possessing a certain elasticity into which glass fibers 116 are incorporated for the purpose of reinforcement, it being of advantage in this case for glass fibers to protrude from the inner wall surface 115a or at least for said fibers to be located in the surface of the inner wall 115a so as to, as a kind of adhesive agent, be able to form together with the plastic material cured within the hose body 115, an intimate and compact composite.

There also exists the possibility of incorporating a glass fiber fabric 118 into the plastic material in lieu of the glass fibers incorporated into the plastic material of the hose body 115; in this embodiment, too, the glass fiber fabric or an incorporated glass fiber mat should be located in the surface of the inner wall of the hose body 115 (FIG. 18). Besides glass fibers, mineral fibers or filaments may be incorporated into the plastic material of the tube-shaped portion 11, by which all fibers are understood which are produced from inorganic materials. However, especially advantageous is here the employment of glass fibers and filaments which may also be incorporated in the form of fabrics or mats into the plastic material of the tube-shaped portion 11 or be present in the form of a glass fiber fabric hose inserted into the plastic hose body. Of particular advantage is the use of glass fiber reinforced thermoplastics which are provided with short glass fibres that are less than 1 mm in length or with glass fibers of up to 3 mm in length, it being possible, however, to also employ glass fibers of a greater length in this case. ABS, polyamides, PC, PE, POM, PP, PS, PVC, SAN, PETP and PBTP may be employed as glass fiber reinforced thermoplastics; essentially those materials or thermoplastic finding employment here which are suitable for the production of the tube-shaped portion 11 for the external fixation apparatus and which, in connection with the proximity of the skin, possess a good dermal compatibility. Fabrics manufactured from glass rovings, glass filaments, glass threads or chopped strand mats may be used as glass fiber fabric. In this case the glass fiber fabrics may possess the most widely varied weaves. Thus, by way of example, two-strand weaves, body weaves and Atlas weaves may be employed; but all other types of suitable weaves may also be used for the fabrication of the glass fiber fabric.

For producing the external fixation apparatus 10, the tube-shaped portion 11 or the tube-shaped portion 211, respectively, which is filled with glass fibers, is filled with a hardenable material subsequent to the application and the fixation of the bone fragments. In particular such plastic materials are used which are quick-curing since it is ensured only by the employment of quick-curing plastic materials that the fixed bone fragments retain their predetermined position after the hardening. In addition, due to the short curing time, the operating surgeon is provided with the possibility of holding the aligned bone fragments in the aligned position without the surgeon suffering from fatigue symptoms which might result in an arrangement of the bone fragments which is no longer in the correct position. Preferably quick-curing material is made use of, it being possible, however, to also employ light in this case for shortening the setting time if an appropriate hardenable material is used. The quick-curing plastic material is prepared outside the fixation apparatus hose by mixing the two components (hardener and plastic material mass) and is then injected into the fixation apparatus hose. It is of advantage if the hose body 212 consists of a transparent or crystal-clear plastic material and if the plastic material to be injected is dyed. When injecting this dyed plastic material mass, it will then be possible to observe the distribution of the mass of plastic material within the inner space of the hose body and to check whether all the sections of the hose body 212 are filled to capacity with plastic material mass.

Instead of the tube-shaped portion 11 used in the embodiment described hereinafter, in the embodiment forms shown in FIGS. 17 and 18 it is also possible to employ tube-shaped portions 211 which possess the construction depicted in the FIGS. 12, 13, 15 and 16 and described in the foregoing.

In the embodiment shown in FIG. 2, the external fixation apparatus 10 consists of a tube-shaped portion 11, the two ends of which 11a,11b are united in a connecting union 16 which is provided with a sealable filling aperture 14. The introduction of the castable or free-flowing plastic material into the inner space of the tube-shaped portion 11 is effected in the direction of the arrow X. The tube-shaped portion 11 is connected with the two bone fragments K1,K2 by means of Kirschner wires, i.e. the tube-shaped portion 11 is secured to the two bone fragments K1,K2 with the aid of these Kirschner wires and this in such a manner that the tube-shaped portion 11 comes to lie a slight distance above the two bone fragments. If several bone fragments have to be fixed, then this tube-shaped portion 11 is routed at different levels and in different directions across the bone fragments, the securing of the tube-shaped portion 11 to the individual bone fragments then being likewise effected via Kirschner wires 30 or by means of other suitable wires or pins, the Kirschner wires then engage on one side of the individual bone fragments and, with their other ends, are connected with that section of the tube-shaped portion 11 which faces the bone fragment to be fixed. Since the tube-shaped portion 11 in the embodiment shown in FIG. 2 is disposed only above and on one side of the bone fragments, the Kirschner wires 30 are secured in the individual bone fragments on one side only. The sections of the Kirschner wires that are passed through the bone fragments are in this case not connected with an appropriate tube-shaped portion 11 with their free ends, however, the possibility of employing two tube-shaped portions 11 exists here as well, of which the one tube-shaped portion 11 comes to lie above the bone fragments to be fixed and the other tube-shaped portion 11 below the bone fragments to be fixed, so that the two tube-shaped portions 11 are then interconnected when the Kirschner wires 30 are at the same time passed through the bone fragments. The disposition of the tube-shaped portion 11 above the bone fragments K1,K2 can be effected in such a way that the Kirschner wires 30 are all introduced into the bone fragments in the same direction. As shown by FIG. 2, the tube-shaped portion 11 can be disposed in such a way that e.g. two Kirschner wires 30 are passed through the section 11c of the tube-shaped portion 11 in the vertical direction, while the other section 11d of the tube-shaped portion 11 is bent aside relative to the section 11c in such a way that the Kirschner wires 30 passed through this hose section 11c come to lie transversely to the longitudinal direction of the Kirschner wires passed through the section 11c of the tube-shaped portion 11c. For such an arrangement and allocation of the two sections 11c,11d of the tube-shaped portion 11, the connecting union 16 employed may then possess an appropriate shape. The tube-shaped portion 11 consists also in this embodiment of a plan fiber-filled plastic material or of a glass fiber fabric embedded in a plastic material, while the tube-shaped portion 11 may also be constructed as a spiral hose. The securing of the tube-shaped portion 11 on the bone fragments K1,K2 may be carried out by means of Kirschner wires 30, but may also be effected with the aid of differently constructed wires, nails or screws.

Figure 3:
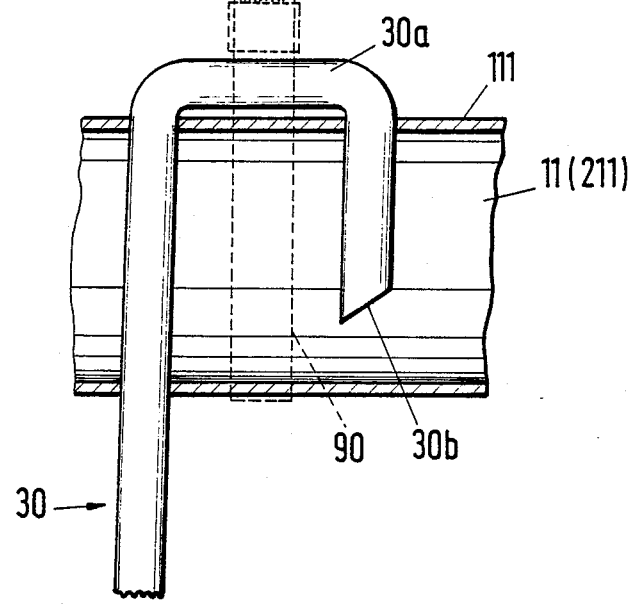
FIG. 3 shows, partly in a view and partly in a vertical section, a Kirschner wire secured to a section of a tube-shaped portion of the external fixation apparatus.

In order to achieve a rotationally stable firm attachment of the Kirschner wires 30 on the tube-shaped portion 11, the free end of each of the Kirschner wires 30 is bent into a U-shape at approximately 180°. This bent wire end is identified by 30a (FIG. 3). The free end 30b of the bent wire section 30a may be constructed in a chamfered manner or extending pointedly so that any easy piercing and insertion into the wall 111 of the tube-shaped portion 11 is possible.

In the embodiment of an external fixation apparatus 10 shown in FIG. 1, a frame 20 is produced from a number of individual interconnected tube-shaped portions 111, in which the two bone fragments K1,K2 are clamped and fixed by means of nails, screws or wires 12. This frame 20 is formed by three longitudinal members 21,22,23, of which, for example, each longitudinal member consists of two interconnected sections. These three longitudinal members 21,22,23 are connected via semicircular members 24,25 within the area of their free ends, the semicircular members likewise consist of two arcuately configured and interconnected sections each. The longitudinal members 21,22,23, the semicircular members 24,25 and the individual sections as well from which the longitudinal members and the semicircular members are made up, are interconnected via ties 26, said ties 26 just as also the connecting union 16 in the external fixation apparatus shown in FIG. 2 being constructed in a tubular fashion. These ties 26 are construction as T-pieces or bends. If two longitudinal member sections are interconnected, then the tie is constructed merely tubularly. It is essential that all tube-shaped portions which are joined in order to form the frame 20 with the aid of the ties 26 be interconnected via these ties 26 in such a way that a freely accessible inner space is provided. For introducing the hardenable material into the inner space of this frame 20 constituted of the various tube-shaped portions 11, a sealable filling aperture is provided which is not depicted in the drawing. However, here too exists the possibility of providing several filling apertures which should then preferably communicate via appropriate connecting tubes with a single filling device so as to ensure a uniform introduction of the hardenable material in order to achieve that, especially when quick-curing plastic materials are involved, plastic material is introduced and contained almost simultaneously within the inner space sections of the frame 20.

In the embodiment shown in FIG. 1, the frame 20 made up of the tube-shaped portion 11 is constructed in such a way that nails, screws or wires 12 can be arranged extending in the vertical direction, in this case the pins 12 extend in the vertical direction and are retained in the longitudinal member 23 embedded in the bone fragments alone, while the pins or nails 12 which are passed through the longitudinal members 21,22 in one plane are passed through the bone fragments K1,K2. However, there also exists the possibility that the two bone fragments K1,K2 being fixed are then surrounded on all sides by the frame 20 so that the nails, pins or screws 12 passed through the bone fragments are, in each case, arranged at both ends in the longitudinal members forming the frame 20.

Apart from this there also exists the possibility of combining into groups several tube-shaped portions 11 of the frame 20, i.e. of the thusly formed hose system, in which the hose system formed by each group is provided with at least one sealable filling aperture for the hardenable material. In all the constructed individual hose systems the filling with hardenable material can be carried out simultaneously or successively at short intervals.

The fracture gap formed between the two bone fragments K1,K2 is indicated at BS in the FIGS. 1 and 2.

Figure 4:
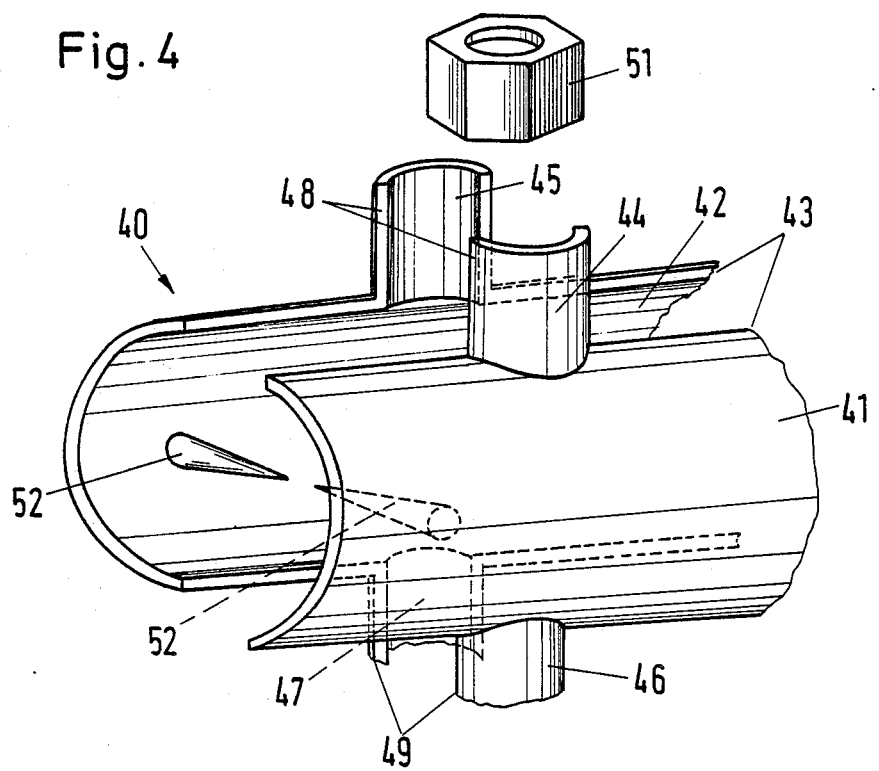
FIG. 4 shows a diagrammatical view of a fixation member.
Figure 5:
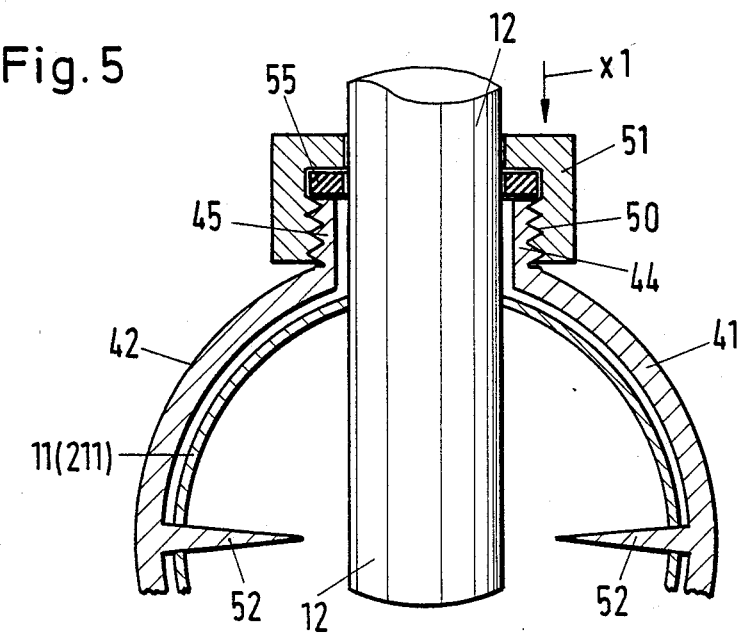
FIG. 5 shows a partial cross section through the fixation member of FIG. 4.

In order to firmly secure the nails or screws on the hose system consisting of the tube-shaped portions 11, a fixation member 40 is provided which possesses the configuration depicted in FIGS. 4 and 5. This fixation member 40 consists of two approximately semicircularly configured shell-shaped parts 41,42 which complement one another so as to form a tubular structural element 43, this tubular structural element 43 has a diameter which corresponds roughly to the external diameter of the tube-shaped portion 11. Apart from the tube-shaped portions 11 having a circular cross section, is also possible to employ tube-shaped portions possessing an oval cross section. The two shell-shaped parts 41,42 of the fixation member 40 forming the tubular structural element 43 are appropriately configured in the external shaping of the tube-shaped portion 11 used.

Each shell-shaped part 41 or 42 of the fixation member 40 possesses on two oppositely located sides molded-on and shell-like configured sections 44,45 or 46,47, which complement one another so as to form two mutually aligned attachment stubs 48,49 and which serve to accommodate a screw or a nail 12. The shell-shaped sections 44,45 or 46,47 are provided on their outer wall with an external thread 50 onto which a coupling nut 51 is screwed. The mounting and attachment of a nail, pin or screw 12 is effected by employing a compression ring 55 which is embraced by the coupling nut 51 screwed onto the external thread of the attachment stub 48 or 49. The disposition of the compression ring 55 has in this case been selected in such a way that the compression ring 55 rests upon the free end of the attachment stub 48 or 49 possessing a circular cross section, so that the screwed-on coupling nut 51 overlaps the compression ring 55. When tightening the coupling nut 51, the compression ring is pressed together in the direction of the arrow X1 with the result that it simultaneously abuts against the outer wall surface of the nail 12, to be more precise, while a pressing effect is develoed so that the nail 12 is retained firmly in the fixation member 40. The wall 111 of the tube-shaped portion 11 arranged within the fixation member 40 is, in the extension of the two attachment stubs 48,49, provided with appropriate openings which may be constructed prior to the insertion of the nail 12. However, since the tube-shaped portion consists of a glass fiber reinforced plastic or of a glass fiber fabric embedded within a plastic possessing a certain capability of elastic restoration, the material of the tube-shaped portion 11 expands in such a way that, when the nail 12 is pressed into the same, the nail 12 can be pressed through the wall 111 of the tube-shaped portion 11 without difficulty so that, in this fashion, also nails having larger diameters can be easily secured. The attachment stubs 48,49 of the fixation member 40 are, as far as their diameters are concerned, adapted to the diameters which the nails or screws used to have. Due to the compression ring 55 used on the attachment stubs 48,49 developing an adequate pressing force when the coupling nuts 51 are tightened, the possibility also exists of securely retaining nails and screws in the attachment stubs 48,49 when the nails or screws 12 employed have a smaller diameter compared with the inner diameter of the attachment stubs 48,49. The attachment stubs 48,49 are constructed in an identical manner and also possess identical cross-sectional surfaces and diameters.

For fixing the tube-shaped portions 11 arranged within the fixation member 40, the shell-shaped parts 41,42 which form the tubular structural element 43, are, on their inner wall surface, provided with fixation studs, spikes or the like 52 which are pressed into the wall 111 of the tube-shaped portion 11 when the fixation member is applied. The number of these fixation studs, spikes or the like 52 can be any number whatever. However, it suffices if, within the area of the two extremities of the fixation member 40, two oppositely located fixation stubs or spikes are provided (FIGS. 4 and 5).

If the fixation member 40 is used in conjunction with pins, nails or wires 12, then the inner wall surfaces of the two attachment stubs 48,49 may be constructed in a plain manner. However, if screws or pins or nails with threads provided at their ends are employed, then it is advantageous if the attachment stubs 48,49 have an internal thread provided on their inner wall surfaces so that an additional securing of the screws 12 is possible. However, since the securing and mounting is effected by means of the compression rings 55, it is not necessary though for the attachment stubs 48,49 to be provided with a thread on their inner wall surfaces. Nails, screws or pins 12 can be retained in a like manner with the fixation member 40.

Figure 6:
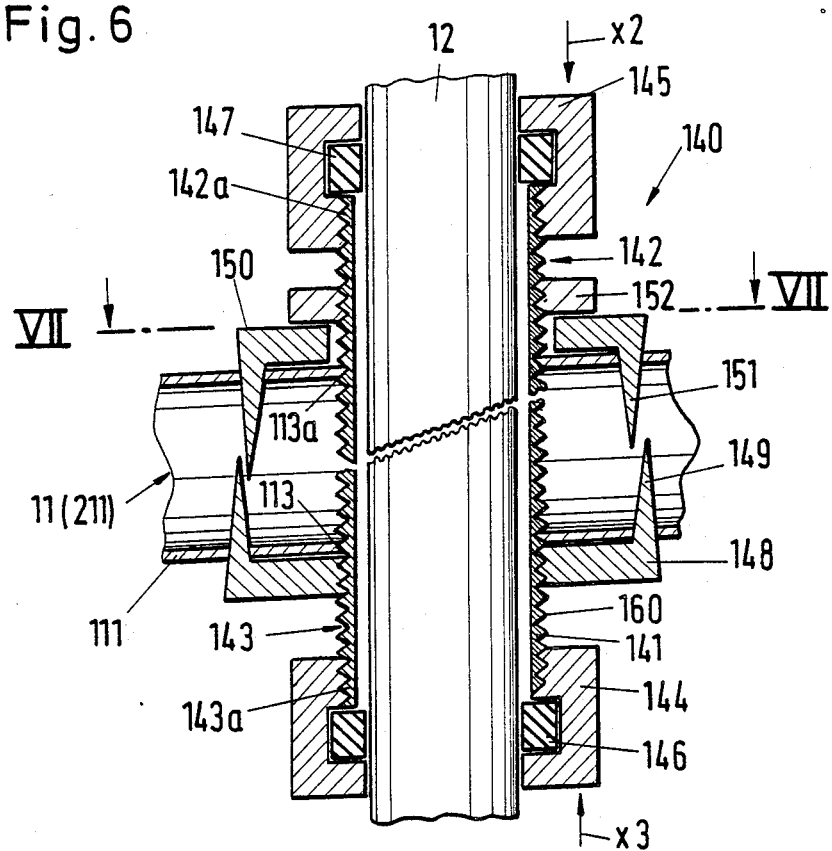
FIG. 6 shows, partly in a view and partly in a vertical section, a further embodiment of the fixation member.

In a further embodiment of a fixation member 40 according to FIG. 6, this fixation member consists of a tube 141 provided with an external thread 160 which, within its inner space, accommodates a nail or a screw 12 for fixation with the bone fragments. This threaded tube 141 is passed through the wall 111 of a tube-shaped portion 11. For this purpose it is advantageous if two mutually aligned perforations 113, 113a are constructed in the wall 111 of the tube-shaped portion 11.

The threaded tube 141 of the fixation member 140 is then arranged within the tube-shaped portion 11 in such a way that the threaded tube 141 projects on both sides with a section 142 or 143, respectively, from this tube-shaped portion 11. The external thread 160 provided on the outer wall surface of the threaded tube 141 may in this case extend over the entire length of the tube 141. However, there also exists the possibility of providing external threads solely within the area of the two extremities 142a,143a of the two threaded tube sections 142,143.

The threaded tube 141 is provided on its sections 142, 143, within the area of their extremities 142a,143a, or on its end, respectively, with one coupling nut 144 or 145 each which engages with the external thread 160 of the threaded tube 141. Each coupling nut 144 or 145 overlaps a compression ring 146 or 147 (FIG. 6) which can be brought into abutment when tightening the coupling nut 144 or 145 fitted to the end of each section 142,143 of the threaded tube 141 provided on the outer wall surface of the nail or screw 12 arranged within the threaded tube 141. On the threaded tube 141, at its extremities, the compression rings 146,147 are then disposed with the coupling nuts 144,145 overlapping them. When tightening the coupling nuts 144,145 in the direction of the arrows X2, X3, the compression rings 146,147 are pressed together in such a way that they are made to abut against the nail or the screw 12. The compression rings 55 and 146,147 consist of suitable deformable material such a rubber or plastics which, if at all possible, does not show any signs of indentation.

In addition, the threaded tube 141 carries a threaded coupling clamp 148 on its section 143 and, on its section 142, an unthreaded coupling clamp 150. The threaded coupling clamp 148 is of annular configuration and is provided with an internal thread so that the coupling clamp 148 can be screwed onto the external thread of the threaded tube 141. This coupling clamp 148 has at least two mutually aligned studs or spikes or the like 149 which point in the direction of the tube-shaped portion 11 and engage into the wall 111 of the tube-shaped portion 11. In order to make sure that the studs, spikes or the like 149 of the coupling clamp 148 engage into the wall 111 of the tube-shaped portion 11, the coupling clamp 148 is not screwed onto the external thread 160 of the threaded tube 141, but, by rotating the threaded tube 141 around its longitudinal axis, the coupling clamp 148 is brought so close to the wall 111 of the tube-shaped portion 11 that the studs, spikes or the like 149 on the coupling clamp 148 engage into the wall 111 of the tube-shaped portion 11.

For this reason the coupling clamp 150 on the section 142 of the threaded tube 141 is not provided with a thread, but this coupling clamp 150, which is likewise of annular configuration, is moved by means of a nut 152 up to the wall 111 of the tube-shaped portion 11. For this purpose the nut 152 is screwed onto the external thread of the threaded tube 141. The coupling clamp 150 also has two mutually aligned studs, spikes or the like 151 which assume the position shown in FIG. 6 and which, when the coupling clamp 150 is brought up to the wall 111 of the tube-shaped portion 11, engage into the wall 111. Following this the two coupling clamps 148,150 are retained on the threaded tube 141 in such a way that their studs, spikes or the like 149,151 are located opposite one another.

This fixation member 140 is used in such a fashion that the threaded tube 141 is passed through appropriately constructed openings in the wall of the tube-shaped portion 11. Following this, the coupling clamps 148,150 are mounted and, by rotating the threaded tube 141, the threaded coupling clamp 148 is moved up to the wall of the tube-shaped portion 11 so that its studs, spikes or the like 149 engage into the wall of the tube-shaped portion 11 or are passed through the wall 111 which, on account of the material used for the tube-shaped portion 111, is possible without afterwards, when the hardenable material is introduced within these areas, material will escape at these puncturing points or is pressed out from these puncturing points.

The unthreaded coupling clamp 150 is mounted on the threaded tube 141 in the same fashion and, by means of the screwed-on nut 152, is moved up to the wall 111 of the tube-shaped portion 11 so that the studs, spikes or the like 151 of the coupling clamp 150 engage into the wall 111 of the tube-shaped portion 11 in the same way as the studs, spikes or the like 149 (FIG. 6).

Figure 7:
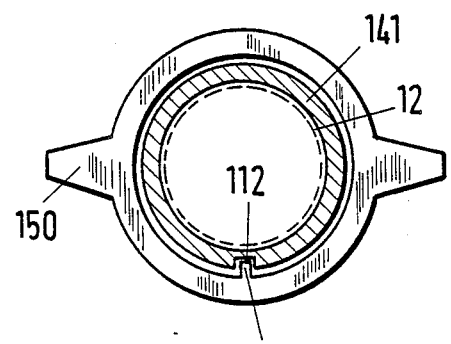
FIG. 7 shows a horizontal section according to Line VII—VII of FIG. 6.
Figure 8:
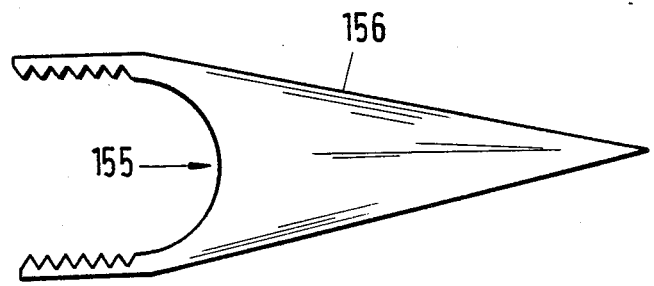
FIG. 8 shows a longitudinal section through a perforator for inserting the threaded tube into the fixation member according to FIG. 6.

Furthermore, the coupling clamp 150 is provided with a rotation-suppressing means, to be more precise, in the form of a cam 154 constructed or formed on the inner wall surface of the coupling clamp 150 which engages into a recess constructed in the outer wall surface of the tube-shaped portion 11 at 112 (FIG. 7). The rotation-suppressing means is in this case located between the coupling clamp 150 and the threaded tube 141 so that, between the nail and the tube-shaped portions 11, after the filling in and curing of the plastic mass, a rotational stability is produced.

For the insertion of the threaded tube 141, a perforator 155 is provided whose point is indicated at 156. This perforator is screwed in for the insertion of the threaded tube 141.

Figure 9:
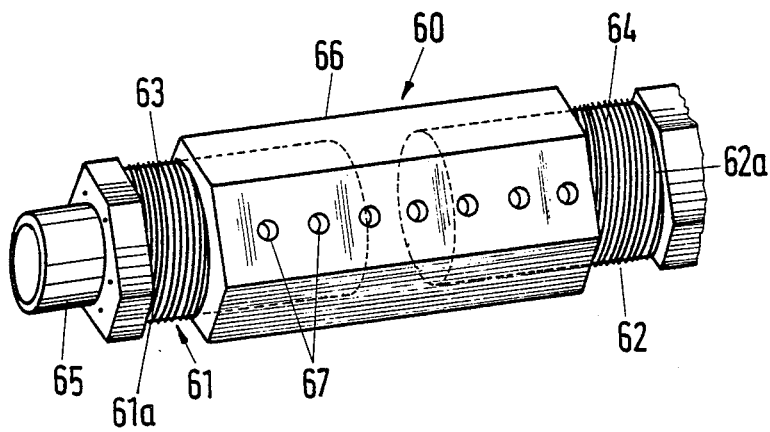
FIG. 9 shows a diagrammatical view of a tightening means.

For the positioning and fixation of bone fragments it is often necessary to construct the external fixation apparatus in such a way that the retightening or a tightening in the first place is possible. For this purpose a tightening means 60 is provided which consists of two tubular sections 61,62 which are closed at their extremities (FIG. 9), said extremities being provided with external threads on their outer wall surfaces. Of the two external threads of the two tubular sections 61,62, one external thread is constructed as a right-handed thread 63 and the other external thread as a left-handed thread 64. Each tubular section 61,62 has, at its external end 61a,62a, an adapter or connecting union 65 for tube-shaped portions 11. These adapters or connecting unions 65 can likewise be constructed along with the tubular sections 61,62 from the same material as these; however, here, too, the possibility exists of employing separate adapters or connecting unions 65 which are then connected with the tubular sections 61,62 while use is being made of suitable connecting means such as e.g. screwed connections. The external diameter of these adapters or connecting unions 65 corresponds to the internal diameter of the tube-shaped portions 11 to be connected.

Figure 10:
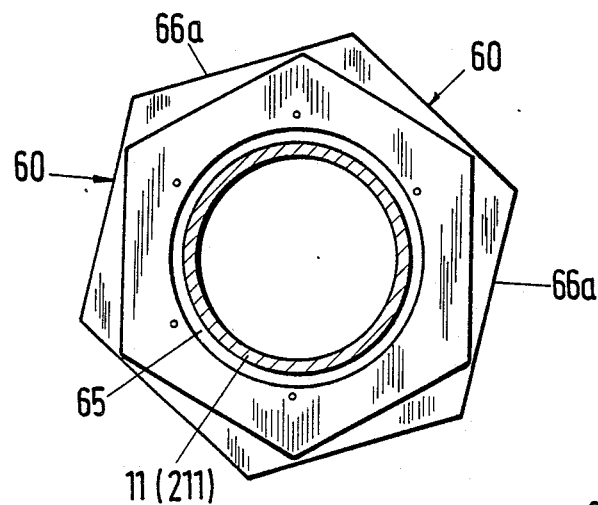
FIG. 10 shows a top view of the tightening means in the direction of its longitudinal axis.
Figure 11:
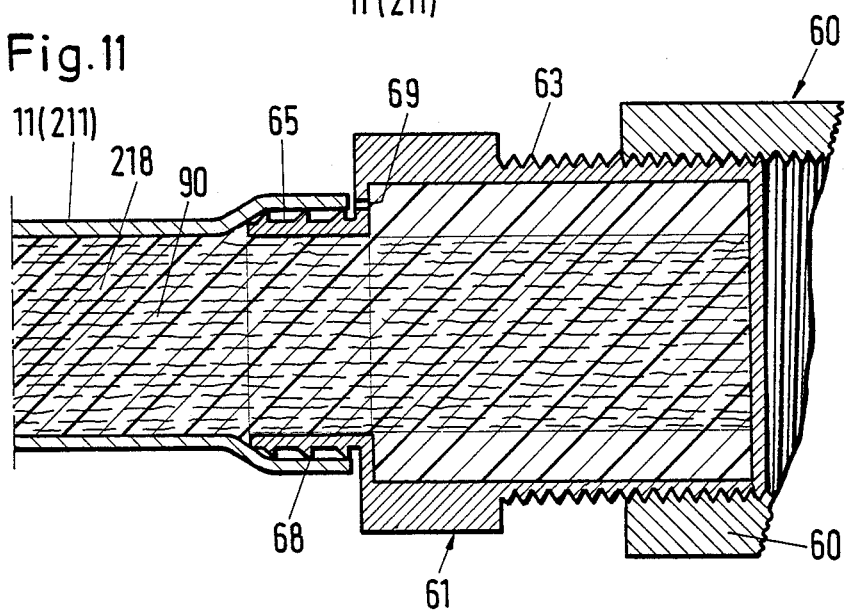
FIG. 11 shows a longitudinal section through a half of the tightening means according to FIG. 9.

A tubular tightening nut 66 is screwed onto the external threads of the two tubular sections 61,62, the outer wall surface of which is provided with a grip grooving or fluting. In the embodiment shown in FIG. 9, the tightening nut 66 is provided with a number of gripping surfaces 66a which are obtained by a hexagonal cross-sectional construction of the tightening nut (FIG. 10). This tightening nut 66 is provided with a number of drilled holes 67 which are arranged in series, i.e. located side-by-side and extend in the longitudinal direction of the tightening nut. These drilled holes 67 serve for the observation and the checking of the tightening path, hence these drilled holes 67 have the function of observation windows. Sections of the outer wall surface of the two tubular sections 61,62 of the tightening means 60 are preferably provided with a different color scheme so that then, with the aid of the colors which can be seen through the drilled holes 67, an evaluation of the tightening path can be made. In order to achieve a secure seating of the tube-shaped portion 11 on the adapter or connecting union 65, these are, on their outer wall surface, provided with a corrugated or ribbed finish which is indicated in FIG. 11 at 68. A ventilation aperture is identified by 69. With a tightening means 60 constructed in this manner a structural element is provided with which a tightening of the tube-shaped portions, e.g. within the frame 20, can be easily effected so that, apart from a tightening, the tightening means at the same time possesses bridging and additional securing properties. The tubular sections 61,62 may also be constructed as hollow screws or banjo bolts, the inner spaces of which are filled with glass fibers, which is effected by a cutting back of the plastic hose body 212 accommodating the filling of glass fiber so that a section of the pure glass fiber filling or of the glass fiber fabric hose is obtained. This section of the glass fiber filling or of the glass fiber fabric hose serves to fill the hollow screw and thus leads to a rigid bond between the tightening means 60 and the fixation apparatus hose after the filling with synthetic resin which, when poured out, flows into the exposed section of the glass fiber filling located within the inner space of the hollow screw. The construction of the tightening means 60 as a hexagon has at the same time the advantage that, with the aid of appropriately constructed tools, it is possible for the tightening means 60 to be seized on the outside and to be turned around its longitudinal axis for tightening.

As fixation apparatus hoses, i.e. as tube-shaped portions 11, it is also possible to employ plastic hoses which, externally or internally, are provided with a glass fiber fabric, these glass fiber fabrics being embedded within the plastic during the manufacture of the hose material from plastic.

When using Kirschner wires 30 it is also of advantage to secure these wires 30 by means of cable ties 80 laid around the fixation apparatus hose and the wires 30 (FIG. 3). The cable ties prevent a sliding out of the wires 30 from their anchoring in the fixation apparatus hose prior to and during the filling of the fixation apparatus hose with synthetic resin.

The fixation member 40,140 and the tightening means 60 consist of suitable plastics of great strength, especially breaking strength; it is possible, however, for other suitable material to be used.

Figure 12:
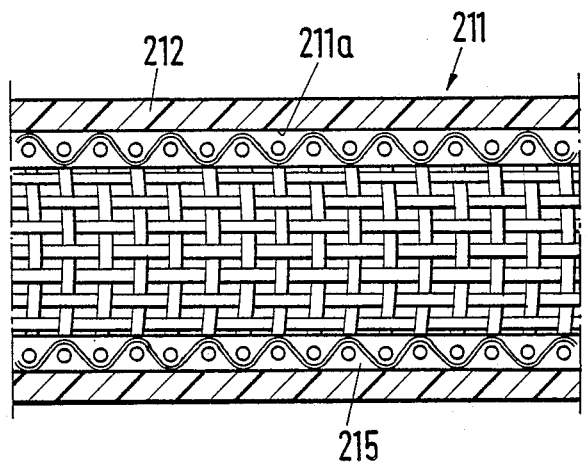
FIG. 12 shows, in an enlarged vertical section, a section of a tube-shaped portion of a hose body fabricated from a plastic with a glass fiber fabric hose inserted into the hose body.
Figure 13:
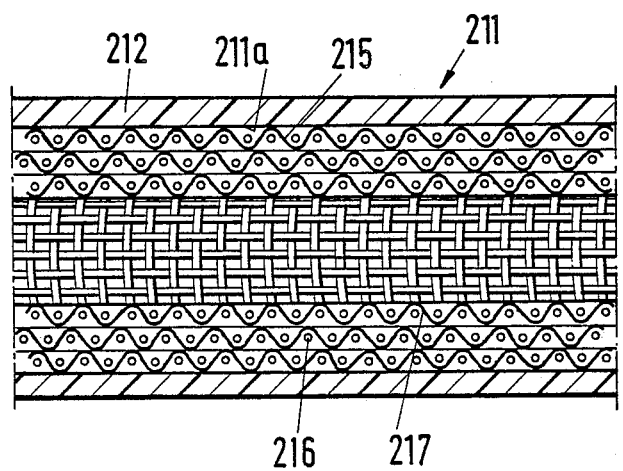
FIG. 13 shows, in an enlarged vertical section, a section of a tube-shaped portion of a hose body fabricated from a plastic with several glass fiber fabric hoses inserted in a layer-like manner.
Figure 14:
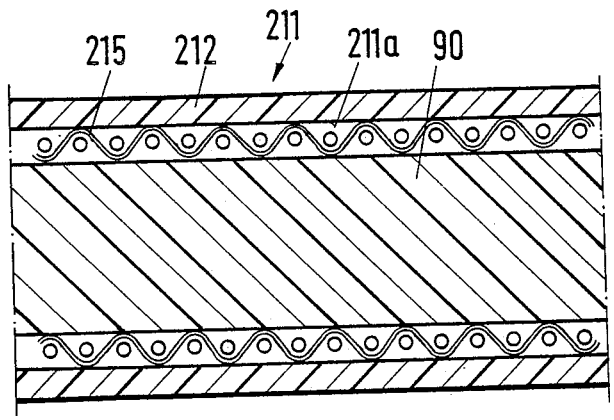
FIG. 14 shows, in an enlarged vertical section, a section of a tube-shaped portion of a hose body fabricated from a plastic with a glass fiber fabric hose inserted into the hose body, with cured plastic disposed within the inner space of the tube-shaped portion.

According to FIGS. 12 and 13, the tube-shaped portion 211 consists of a hose body 212 that is fabricated from a flexible plastic. A hose 215 fabricated from glass fiber fabric is inserted into the inner space of the hose body 212 which rests against the inner wall of the hose body 212. If use is made of a hose system consisting of several tube-shaped portions 211, then the glass fiber fabric hoses are inserted into the individual hose sections prior to the hose sections being joined together and interconnected. It is also possible to use longer dimensioned hose bodies 212 with inserted glass fiber fabric hose 215 that are cut to the required lengths for use.

A glass fiber fabric 215 may be inserted into the inner space of the hose body 212 (FIG. 12), but several glass fiber fabric hoses 215,216,217 may also be inserted thus forming several layers (FIG. 13). Depending on the requirements, the glass fiber fabric hoses may have different wall thicknesses. A thusly constructed tube-shaped portion 211 is then filled with the hardenable plastic. In FIG. 4, the cured plastic is indicated at 90. The advantage consists in that such a fixation apparatus hose can be sterilized prior to use. Also the glass fiber fabric hose can be sterilized prior to its insertion into the hose body. The tube-shaped portion 211 thus has the function of a mold. After the effected introduction into the hose system, the hardenable plastic penetrates into the glass fiber fabric of the glass fiber fabric hose and flows through the glass fibers so that, following the curing, a rigid intimate bond between the glass fiber fabric and the plastic is produced. The external hose body fabricated from plastic merely has a holding-together function and serves to effect the external delimitation and may, therefore, be constructed with thin walls. In this way a composite of great stability is obtained. This stability is adjustable by employing a varying number of glass fiber fabric hose layers.

Figure 15:
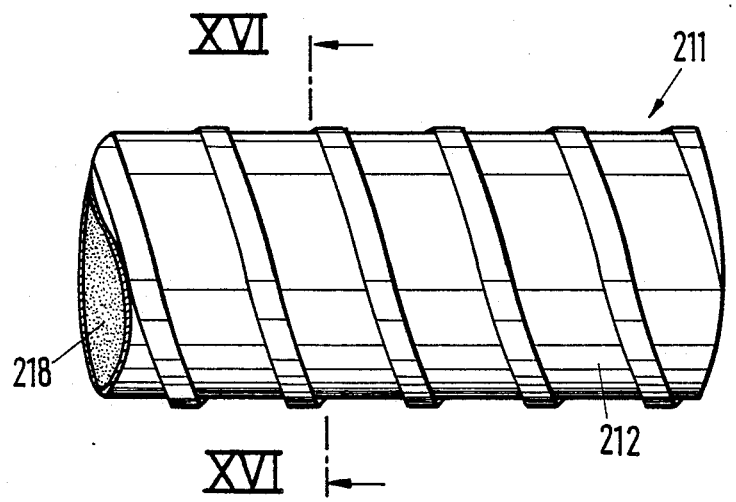
FIG. 15 shows, in an enlarged vertical section, a section of a tube-shaped portion of a spiral hose body filled with a glass fiber fabric.
Figure 16:
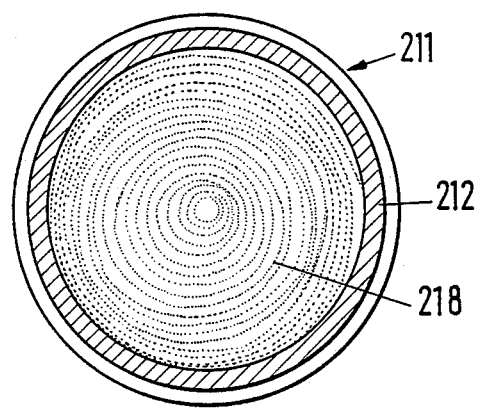
FIG. 16 shows a vertical section according to Line XVI—XVI in FIG. 15.

According to the FIGS. 15 and 16, the hose body 212 is of spiral configuration and consists preferably of a transparent or crystal-clear plastic. The inner space of the hose body 212 is provided with a glass fiber filling 218 which consists of a rolled-up glass fiber fabric mat or of several glass fiber fabric hoses inserted into one another. This glass fiber filling 218 fills the inner space of the hose body 212.

I claim:

1. An external bone fixation apparatus, comprising at least one flexible tube-shaped portion which is externally arrangeable on a patient, opposite bone fragments to be fixed; and connecting means securable in the bone fragments for connecting with the at least one flexible tube-shaped portion, the tube-shaped portion being filled with a hardenable material which, subsequent to hardening thereof, forms a rigid frame with the connecting means so as to hold the bond fragments in a desired position to enable healing thereof, the tube-shaped portion being formed of a glass fiber-reinforced material, and one of transparent and clear plastic in the shape of a spiral tube having a bead-like reinforcement which is arranged in a closed tube system, the hardenable material being a quick-curing plastic which is filled into the interior of the closed tube system.

2. An external bond fixation apparatus, comprising at least one flexible tube-shaped portion which is externally arrangeable on a patient, opposite bone fragements to be fixed; and connecting means securable in the bone fragments for connecting with the at least one flexible tube-shaped portion, the tube-shaped portion being filled with a hardenable material which, subsequent to hardening thereof, forms a rigid frame with the connecting means so as to hold the bone fragments in a desired position to enable healing thereof, wherein the tube-shaped portion is formed of a tube body of one of a transparent and a clear plastic filled with glass fibers so as to form a spiral tube having a bead-like reinforcement arranged in a closed tube system, the hardenable material being a quick-curing plastic filled into the interior of the closed tube system.

3. An external bond fixation apparatus, comprising:
at least one flexible tube-shaped portion which is externally arrangeable on a patient, opposite bone fragments to be fixed; and
connecting means securable in the bone fragments for connecting with the at least one flexible tube-shaped portion, the tube-shaped portion being filled with a hardenable material which, subsequent to hardening thereof, forms a rigid frame with the connecting means so as to hold the bone fragments in a desired position to enable healing thereof, wherein the tube-shaped portion is formed of a glass fiber fabric embedded in one of a transparent and a clear plastic and is formed as a spiral tube having a bead-like reinforcement which is arranged in a closed tube system, the hardenable material being a quick-curing plastic filled into the interior of the closed tube system.

4. An external fixation apparatus according to claim 2, wherein the glass fiber filling of the tube body consists of one of at least one hose inserted into the tube body and a glass fiber mat rolled so as to form a tube.

5. An external fixation apparatus according to claim 1, and further comprising a connecting union having a sealable filling aperture, the connecting union being provided so as to interconnect the ends of the tube-shaped portion.

6. An external fixation apparatus according to claim 5, wherein the connecting union has one of a Y-shape and a T-shape.

7. An external fixation apparatus according to claim 5, wherein several tube-shaped portions are joined together so as to form a frame, additional connecting unions being provided so as to interconnect the tube-shaped portions so that the interior of all the tube-shaped portions intercommunicate.

8. An external fixation apparatus according to claim 7, wherein the several tube-shaped portions are combined into groups, each group of tube-shaped portions being provided with at least one sealable filling aperture for the hardenable material.

9. An external fixation apparatus according to claim 1, wherein the connecting means is provided so as to route the tube-shaped portion in various planes and directions across the bone fragments.

10. An external fixation apparatus according to claim 1, wherein the connecting means includes wires, each of the wires having an end which is bent aside approximately 180°, and is thrustable into the tube-shaped portion and connectable thereto in a rotationally stable manner.

11. An external fixation apparatus according to claim 10, wherein the fixation wires are Kirschner wires, and further comprising cable ties for retaining the Kirschner wires on the tube-shaped portion.

12. An external fixation apparatus according to claim 1, wherein the connecting means includes a fixation member and one of screws and nails, the fixation member being arranged so as to secure the screws and nails to the tube-shaped portion.

13. An external fixation apparatus according to claim 12, wherein the fixation member is formed of a tube provided with an external thread and passed through to opposing and mutually aligned perforations in the wall of the tube-shaped portion, the tube of the fixation member having an inner space which accommodates one of the nail and screw, the threaded tube being provided so as to have a section which projects on both sides from the tube-shaped portion, a coupling nut being provided on a each of these projecting sections so as to engage with the external thread of the threaded tube, the coupling nuts each overlapping a compression ring provided on the outer wall surface of the nail and screw arranged within the threaded tube, the compression ring being brought into abutment with tightening of the coupling nut fitted to each end of the projecting sections of the threaded tube, a threaded coupling clamp being provided on a section of the threaded tube facing the bone fragments, the threaded coupling clamp being seated on the external thread with a stud or spike engaging into the wall of the tube-shaped portion, an unthreaded coupling clamp with a stud or spike being provided on another section of the threaded tube so that the stud or spike engages into the wall of the tube-shaped portion, a nut being provided so as to retain the unthreaded coupling clamp on the threaded tube, and a cam being arranged so as to connect the unthreaded coupling clamp with the threaded tube in a rotationally stable manner.

14. An external fixation apparatus according to claim 12, wherein the fixation member is made up of two shell-shaped parts arranged so as to encase the tube-shaped portion and compliment one another so as to form a tubular structural element, each shell-shaped part having on at least two oppositely located sides shell-like configured sections which compliment one another so as to form two mutually aligned attachments stubs which serve to receive one of the screw and nail, the shell-shaped sections being provided on their outer wall with an external thread, a compression ring being fitted onto the end of the attachment stub and a coupling nut being provided on the external thread of the shell-shaped sections so as to overlap the compression ring.

15. An external fixation apparatus according to claim 14, wherein each of the shell-shaped parts has an inner wall provided with at least two studs or spikes.

16. An external fixation apparatus according to claim 1, and further comprising tightening means provided for each tube portion which spans a fracture.

17. An external fixation apparatus according to claim 16, wherein the tightening means includes two tubular sections provided with external threads on their outer wall surfaces, one of the external threads being a right-handed thread and the other external thread being a left-handed thread, each of the tubular sections have an external end on which a connecting union is provided for the tube-shaped portions, a tubular tightening nut is provided so as to be screwed onto the external threads of the two tubular sections and has one of a grip grooving and fluting finish, as well as a number of poles arranged therein in a side-by-side manner.

18. An external fixation apparatus according to claim 17, wherein the two tubular sections of the tightening means have an outer wall with sections of different colors.

19. An external fixation apparatus according to claim 17, wherein ventilation apertures are provided in the wall of the tubular sections of the tightening means.

20. An external fixation apparatus according to claim 1, wherein the connecting means includes at least one of wires, nails and pins, the wires having bent-aside ends thrust into the wall of the tube-shaped portion, the connecting means further including cable ties arranged so as to secure the bent-aside wire ends to the tube-shaped portion.

21. An external fashion apparatus according to claim 1, wherein at least one hose fabricated of a glass fiber fabric is inserted into the tube body of the tube-shaped portion so that the tube body with the at least one glass fiber fabric hose and the hardenable material cured within the interior of the tube-shaped portion form a composite.

22. An external fixation apparatus according to claim 21, wherein the glass fiber hoses have identical thicknesses.

23. An external fixation apparatus according to claim 21, wherein the glass fiber hoses have varying thicknesses.

24. An external fixation apparatus according to claim 21, wherein the at least one hose includes several glass fiber fabric hoses inserted into one another.

25. An external fixation apparatus according to claim 21, wherein the at least one hose is a glass fiber fabric mat rolled up so as to form a hose.

26. An external fixation apparatus according to claim 1, wherein the hardenable material is provided with a color.

* * * * *